(12) United States Patent
Miyama et al.

(10) Patent No.: US 10,327,964 B2
(45) Date of Patent: Jun. 25, 2019

(54) DISPOSABLE DIAPER

(71) Applicant: UNICHARM CORPORATION, Ehime (JP)

(72) Inventors: Takuya Miyama, Kanonji (JP); Satoru Sakaguchi, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 0 days.

(21) Appl. No.: 16/072,577

(22) PCT Filed: Jan. 13, 2017

(86) PCT No.: PCT/JP2017/000952
§ 371 (c)(1),
(2) Date: Jul. 25, 2018

(87) PCT Pub. No.: WO2017/135010
PCT Pub. Date: Aug. 10, 2017

(65) Prior Publication Data
US 2019/0083328 A1    Mar. 21, 2019

(30) Foreign Application Priority Data

Feb. 1, 2016 (JP) .................... 2016-017174

(51) Int. Cl.
*A61F 13/49* (2006.01)
*A61F 13/496* (2006.01)
(Continued)

(52) U.S. Cl.
CPC .... *A61F 13/4963* (2013.01); *A61F 13/49413* (2013.01); *A61F 2013/1504* (2013.01); *A61F 2013/49082* (2013.01)

(58) Field of Classification Search
CPC .............. A61F 13/493; A61F 13/49413; A61F 13/49466; A61F 13/4963; A61F 2013/1504; A61F 2013/49068; A61F 2013/49082
See application file for complete search history.

(56) References Cited

U.S. PATENT DOCUMENTS 5,358,500 A * 10/1994 Lavon ............... A61F 13/49011
604/358
5,707,364 A * 1/1998 Coates .............. A61F 13/49004
604/385.01
(Continued)

FOREIGN PATENT DOCUMENTS

CN      104619298 A      5/2015
CN      104780880 A      7/2015
(Continued)

OTHER PUBLICATIONS

International Search Report in PCT/JP2017/000952, dated Mar. 28, 2017.
(Continued)

*Primary Examiner* — Catharine L Anderson
(74) *Attorney, Agent, or Firm* — Hauptman Ham, LLP (57) ABSTRACT

A front edge of a disposable diaper includes a curved recess recessed rearward in a region including the center of the disposable diaper in a width direction, and a front straight portion extending parallel to the width direction from the outer edge of the recess. A rear edge of the disposable diaper includes a curved projection protruding rearward in the region, and a rear straight portion extending parallel to the width direction from the outer edge of the projection. A pair of first cutout portions is recessed rearward from the outer edge of the front straight portion and recessed inward from the front edge of the outer edge of the disposable diaper. A pair of second cutout portions is recessed frontward from the
(Continued)

outer edge of the rear straight portion and recessed inward from the rear edge of the outer edge of the disposable diaper.

9 Claims, 5 Drawing Sheets

(51) Int. Cl.
*A61F 13/494* (2006.01)
*A61F 13/15* (2006.01)

(56) References Cited

U.S. PATENT DOCUMENTS

| | | | |
|---|---|---|---|
| 7,361,167 B2* | 4/2008 | Erickson | A61F 13/15747 604/385.01 |
| 8,092,439 B2 | 1/2012 | Stabelfeldt et al. | |
| 9,241,842 B2* | 1/2016 | Roe | A61F 13/49014 |

FOREIGN PATENT DOCUMENTS

| | | |
|---|---|---|
| DE | 20216466 U1 | 2/2003 |
| JP | S62-136505 U | 8/1987 |
| JP | H8-510942 A | 11/1996 |
| JP | 2008-525162 A | 7/2008 |
| JP | 2010-131111 A | 6/2010 |
| JP | 2014-204754 A | 10/2014 |
| WO | 2015/046633 A1 | 4/2015 |

OTHER PUBLICATIONS

Extended European Search Report in EP Application No. 17747172.9, dated Dec. 6, 2018, 7pp.

Office Action in CN Application No. 201780009341.7, dated Feb. 3, 2019, 14pp.

* cited by examiner

DISPOSABLE DIAPER

RELATED APPLICATIONS

The present application is a National Phase of International Application Number PCT/JP2017/000952, filed on Jan. 13, 2017, and claims priority to Japanese Application No. 2016-017174, filed on Feb. 1, 2016.

TECHNICAL FIELD

The present invention relates to a disposable diaper.

BACKGROUND ART

Generally, a navel part of an infant (particularly, a newborn baby) is in a state like a scratch because a skin surface is not dry. Therefore, when an end of a disposable diaper in a longitudinal direction touches the navel part of the infant, there has been concern that it will hurt the navel of the infant and give pain to the infant.

In a disposable diaper, in order to protect such delicate infant's navel, a disposable diaper having a recess in a center of a width direction of the disposable diaper in a front waistline region is known. The center of the front edge of the disposable diaper in the width direction is a recess recessed inward in the longitudinal direction, and the side portion of the front edge in the width direction protrudes outward in the longitudinal direction (see, for example, Patent Literature 1, FIGS. 6 and 8).

CITATION LIST

Patent Literature

Patent Literature 1: JP 2008-525162 A

SUMMARY OF INVENTION

In a disposable diaper of Patent Literature 1, as illustrated in FIG. 6, continuous sheets in which a front waistline region, a crotch region, and a rear waistline region in a plurality of disposable diapers are continued in a longitudinal direction are conveyed, and the continuous sheets are cut with a cutting line extending in the width direction, thereby manufacturing the disposable diapers. The front edge of one disposable diaper is the rear edge of the adjacent disposable diaper. Therefore, the center of the rear edge of the disposable diaper in the width direction protrudes outward in the longitudinal direction, and the side portion of the rear edge in the width direction is recessed inward in the longitudinal direction.

Since the side portion of the rear edge of the disposable diaper in the width direction has a shape recessed inward in the longitudinal direction, the outer edge at the rear edge protrudes from the recessed bottom and has a pointed shape toward the outside in the longitudinal direction. Since the rear edge of the disposable diaper has a pointed shape toward the outside in the longitudinal direction, there has been concern that the pointed portion will damage the body of the delicate infant and give pain to the infant.

As a result of earnest research by the present applicant, it has been found that the pointed shape is generally easy to unconsciously notice, and in particular, women such as mothers have a high attention to the sharp shape. When the mother is conspicuous in the pointed shape toward the outside of the longitudinal direction in the disposable diaper, it is concerned about the stimulation to the infant's skin and it may become a stress.

Therefore, the present invention has been made in view of such a situation, and it is an object of the present invention to provide a disposable diaper which can protect a navel while suppressing the stimulation to a wearer's skin and can reduce stress of a mother against the stimulation to the skin.

A disposable diaper (disposable diaper 10) according to the present disclosure including: a front waistline region (front waistline region 20), a rear waistline region (rear waistline region 30), and a crotch region (crotch region 25) positioned between the front waistline region and the rear waistline region; a longitudinal direction extending (longitudinal direction L) from the front waistline region to the rear waistline region and a width direction (width direction W) perpendicular to the longitudinal direction; and a pair of fastening tapes (fastening tapes 90) extending in the width direction in the rear waistline region and fastened to the front waistline region, wherein the front edge (front edge 11) of the disposable diaper includes a curved recess (recess 111) recessed rearward in a region including the center of the disposable diaper in the width direction, and a front straight portion (front straight portion 112) extending parallel to the width direction from the outer edge of the recess, and the rear edge (rear edge 12) of the disposable diaper includes a curved projection (projection 121) protruding rearward in the region including the center of the disposable diaper in the width direction, and a rear straight portion (rear straight portion 122) extending parallel to the width direction from the outer edge of the projection, the disposable diaper including: a pair of first cutout portions (first cutout portions 15) recessed rearward in a curved shape from the outer edge of the front straight portion and recessed inward in the width direction in a curved shape from the front edge of the outer edge of the disposable diaper; and a pair of second cutout portions (second cutout portions 16) recessed frontward in a curved shape from the outer edge of the rear straight portion and recessed inward in the width direction in a curved shape from the rear edge of the outer edge of the disposable diaper.

DESCRIPTION OF EMBODIMENTS

At least the following matters will become apparent from the description of this specification and the accompanying drawings.

A disposable diaper including;

a front waistline region, a rear waistline region, and a crotch region positioned between the front waistline region and the rear waistline region;

a longitudinal direction extending from the front waistline region to the rear waistline region and a width direction perpendicular to the longitudinal direction; and a pair of fastening tapes extending in the width direction in the rear waistline region and fastened to the front waistline region, wherein the front edge of the disposable diaper includes a curved recess recessed rearward in a region including the center of the disposable diaper in the width direction, and a front straight portion extending parallel to the width direction from the outer edge of the recess, and the rear edge of the disposable diaper includes a curved projection protruding rearward in the region including the center of the disposable diaper in the width direction, and a rear straight portion extending parallel to the width direction from the outer edge of the projection, the disposable diaper including:

a pair of first cutout portions recessed rearward in a curved shape from the outer edge of the front straight portion and recessed inward in the width direction in a curved shape from the front edge of the outer edge of the disposable diaper; and a pair of second cutout portions recessed frontward in a curved shape from the outer edge of the rear straight portion and recessed inward in the width direction in a curved shape from the rear edge of the outer edge of the disposable diaper.

According to such a disposable diaper, the curved recess in the front waistline region can protect the navel while suppressing the stimulation to the wearer's skin. The ventral side of the wearer has an inflated shape as compared with the dorsal side, and the front edge of the disposable diaper is arranged therein. The front edge of the disposable diaper is arranged with a cutout portion and a front straight portion extending parallel to the width direction and does not protrude outward in the longitudinal direction. Therefore, there is little stimulation when the front edge of the disposable diaper hits the inflated belly of the wearer, and it is possible to protect the delicate infant's skin. In addition, a spine is arranged in the center of the back of the wearer, and the center of the back of the wearer is recessed towards the ventral side from the left and right parts. The concave portion (rhombus of Michael) is a recess of a sacrum portion, and the projection is arranged therein. It is possible to cover the concave portion of the back and both sides thereof by the projection and the rear straight portion and prevent leakage on the dorsal side. The rear edge of the disposable diaper is arranged with a projection and a rear straight portion extending parallel to the width direction and does not protrude outward in the longitudinal direction. Therefore, there is little stimulation when the wearer is placed on the rear waistline region at the time of wearing and the rear edge of the disposable diaper hits the back of the wearer, and it is possible to protect the delicate infant's skin.

In addition, a first cutout portion and a second cutout portion constituting four corners of the disposable diaper are recessed inward in the longitudinal direction in a curved shape and are recessed inward in the width direction in a curved shape. Therefore, the first cutout portion and the second cutout portion do not have a pointed shape on the outer side in the longitudinal direction and can suppress the stimulation to the skin by the first cutout portion and the second cutout portion. In addition, the front edge of the disposable diaper and the rear edge of the disposable diaper are arranged to overlap each other in a state in which the fastening tape is fastened. At this time, since the first cutout portion and the second cutout portion are recessed inward in the width direction, the outer edge of the rear edge of the disposable diaper does not overlap the outer edge of the front edge of the disposable diaper and is easily arranged spaced apart in the width direction. Therefore, air permeability is improved, steam is suppressed, and skin troubles such as eczema can be suppressed. In a case where the outer edge of the rear edge of the disposable diaper overlaps the outer edge of the front edge of the disposable diaper, since the first cutout portion is covered with the rear waistline region, it tends to directly touch the wearer's skin. Since the first cutout portion has a curved concave shape, the stimulation to the skin at the time of wearing can be suppressed. In addition, the four corners, the front edge, and the rear edge of the disposable diaper are not provided with a pointed shape on the outer side in the longitudinal direction, mothers have an overall gentle impression of the disposable diapers on the skin and can reduce the stress to the skin stimulation.

Such a disposable diaper includes a first intersection portion where the recess and the front straight portion intersect with each other and a second intersection portion where the projection and the rear straight portion intersect with each other, and it is preferable that the first intersection portion and the second intersection portion have a curved shape.

According to such a disposable diaper, since the first intersection portion and the second intersection portion have a curved shape, it is possible to suppress the stimulation to a delicate navel or a hard portion of a spine.

In such a disposable diaper, the outer edge of the disposable diaper includes a leg surrounding opening arranged around the wearer's leg, a front flap portion arranged in front of the leg surrounding opening, and a rear flap portion arranged at a rear side of the leg surrounding opening, and it is preferable that a third intersection portion where the leg surrounding opening and the front flap portion intersect and a fourth intersection portion where the leg surrounding opening and the rear flap portion intersect have a curved shape.

According to such a disposable diaper, the third intersection portion and the fourth intersection portion may have a curved shape, and pointed corners are not formed at the front edge and the rear edge of the leg surrounding opening. Even when the wearer moves the legs and the leg surrounding opening strongly hits the wearer, it is possible to suppress the stimulation to the portion around the wearer's legs.

In such a disposable diaper, it is preferable that the fourth intersection portion is positioned outside the third intersection portion in the width direction.

In the third intersection portion and the fourth intersection portion where the leg surrounding opening and the flap portion intersect, both the force related to the flap portion and the force related to the leg surrounding are applied, and thus the forces tend to concentrate. According to such a disposable diaper, the position of the third intersection portion in the width direction and the position of the fourth intersection portion in the width direction are not arranged on a straight line extending in parallel to the longitudinal direction, and the force applied to the third intersection portion and the force applied to the fourth intersection portion hardly concentrate, thereby suppressing the stimulation to the skin due to the concentration of the force.

Since the fourth intersection portion is positioned on the outer side in the width direction than the third intersection portion, the region between the right and left leg surrounding openings is wider at the rear side than at the front side. Since the region between the leg surrounding openings in the rear waistline region is relatively wide, the wearer does not protrude from the rear waistline region at the time of wearing, and it is possible to lay down the wearer in the rear waistline region. Therefore, it is possible to wear the disposable diaper without stimulating the wearer. In addition, since the region between the leg surrounding openings in the front waistline region is relatively narrow, the wearer can wear the disposable diaper without giving the stimulation to the legs when the front waistline region is applied to the belly through the front waistline region between the wearer's legs at the time of wearing.

In such a disposable diaper, the first cutout portion includes a first extension portion extending rearward from the front straight portion, the second cutout portion includes a second extension portion extending frontward from the rear straight portion, an angle formed by the front straight portion and the first extension portion is an obtuse angle, an angle formed by the rear straight portion and the second extension portion is an acute angle, and a fifth intersection portion where the rear straight portion and the second extension portion intersect may have a pointed shape toward the outside in the width direction.

According to such a disposable diaper, since the first cutout portion positioned at the front edge of the disposable diaper has an obtuse angle, it is possible to suppress the stimulation to the skin. In addition, it gives an impression that it is gentle to the wearer's belly, and stress of the mother on the stimulation to the skin can be reduced. In addition, the second cutout portion positioned at the front edge of the disposable diaper is arranged to overlap the front waistline region when the fastening tape is fastened, and does not directly touch the wearer's skin. Therefore, the stimulation to the wearer's skin can be prevented even if the fifth intersection portion where the rear edge of the disposable diaper and the second cutout portion intersect has an acute angle.

In such a disposable diaper, the first cutout portion includes a first extension portion extending rearward from the front straight portion, the second cutout portion includes a second extension portion extending frontward from the rear straight portion, and the first extension portion and the second extension portion may extend parallel to the longitudinal direction.

When manufacturing such a disposable diaper, continuous sheets in which a front waistline region, a crotch region, and a rear waistline region in a plurality of disposable diapers are continued in a longitudinal direction are conveyed, and the continuous sheets are cut with a cutting line extending in the width direction, thereby manufacturing the plurality of disposable diapers. In a state of the continuous sheet in the manufacturing method, the first extension portion and the second extension portion are continuous, and the first extension portion of one disposable diaper and the second extension portion of the adjacent disposable diaper are formed by cutting at the cutting line. Since the first extension portion and the second extension portion are parallel to the longitudinal direction, even when the cutting position deviates in the longitudinal direction during the manufacture, it is possible to prevent an unintentional formation of an acute angle in the first cutout portion and the second cutout portion, without a change in the angle of the first cutout portion and the second cutout portion, In such a disposable diaper, it is desirable to include a waist stretchable portion which is arranged in the rear waistline region of the disposable diaper and expands and contracts in the width direction.

According to such a disposable diaper, the rear waistline region is contracted by the waist stretchable portion, and wrinkles extending in the longitudinal direction are formed.

In the rear waistline region, undulations that float in the thickness direction due to wrinkles are formed. The undulation makes it difficult for a pointed portion in the first cutout portion, the second cutout portion, and the like of the disposable diaper to be conspicuous, the disposable diaper exerts a visual effect that gives a gentle impression to the skin as a whole, and mothers feel less stressful to the stimulation to the skin.

In such a disposable diaper, a folding line extending in the width direction is provided in the crotch region, and a distance in the longitudinal direction between the folding line and the width direction center of the projection is longer than a distance in the longitudinal direction between the folding line and the width direction center of the recess.

According to such a disposable diaper, the projection extends outward in the longitudinal direction than the recess in a state of being folded with the folding line as a base point. In a state in which a plurality of disposable diapers are stacked, a wearing assistant such as a mother can easily take out the disposable diaper by gripping the projection.

Such a disposable diaper includes:

a back film arranged on the non-skin surface side of the absorber; and an exterior sheet made of a nonwoven fabric and positioned on the non-skin surface side of the back film, wherein the front edge of the back film is preferably positioned at a rear side of the front edge of the disposable diaper, and the rear edge of the back film is preferably positioned at a front side of the rear edge of the disposable diaper.

According to such an absorbent article, air permeability of the front edge and the rear edge of the disposable diaper is improved and steam is reduced, so that delicate skin of the infant can be protected.

Regarding Disposable Diaper According to the Present Embodiment

Next, an embodiment of a disposable diaper 10 according to the present invention will be described with reference to the drawings. In the following description of the drawings, the same or similar reference numerals are assigned to the same or similar parts. However, it should be noted that the drawings are schematic and ratios of dimensions and the like may be different from actual ones. Therefore, concrete dimensions and the like should be determined with reference to the following explanation. In addition, the drawings may include portions having different dimensional relationships or ratios.

(1) Overall Schematic Configuration of Disposable Diaper

Figure 1:
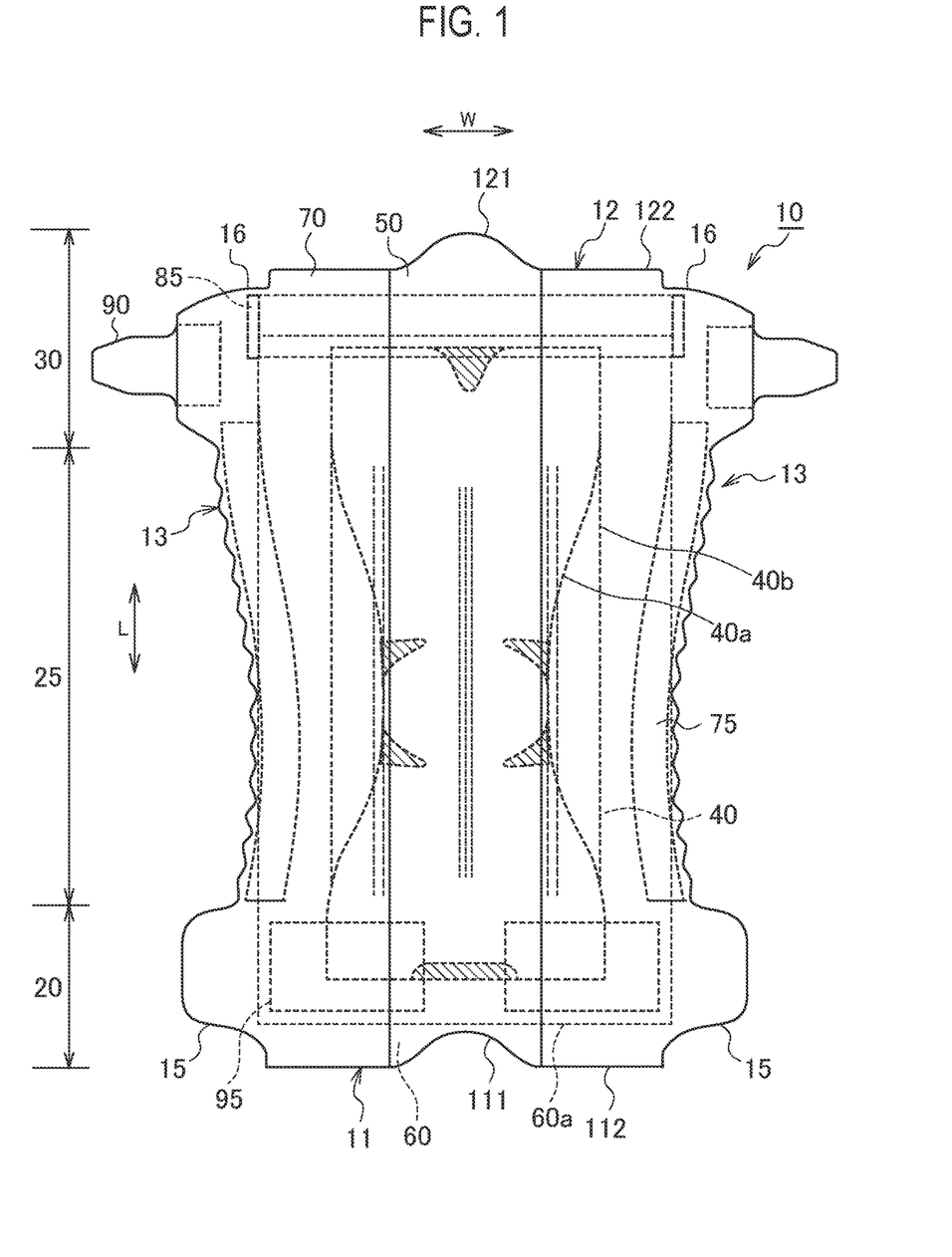
FIG. 1 is a developed plan view of a disposable diaper according to the present embodiment.

FIG. 1 is a developed plan view of a disposable diaper 10 according to the present embodiment. The developed view illustrated in FIG. 1 is a view illustrating a state in which a leg stretchable portion 75 is stretched to a state in which wrinkles are not formed in a top sheet 50, a side flaps 70, and the like constituting the disposable diaper.

The disposable diaper 10 includes a front waistline region 20, a crotch region 25, and a rear waistline region 30. The front waistline region 20 is a portion which is in contact with the front waistline portion (belly portion) of the wearer. In addition, the rear waistline region 30 is a portion which is in contact with the rear waistline portion (back portion) of the wearer. The crotch region 25 is positioned between the front waistline region 20 and the rear waistline region 30. In the present embodiment, the direction from the front waistline region 20 to the rear waistline region 30 is referred to as the longitudinal direction L, and the direction perpendicular to the longitudinal direction L is referred to as the width direction W.

The disposable diaper 10 includes an absorber 40. The absorber 40 includes an absorbent core 40a and a core wrap 40b. The absorbent core 40a is the same as the conventional disposable diaper and can be appropriately constituted by using known members or materials, such as ground pulp and super-absorbent polymer. The absorbent core 40a is wrapped by a sheet-shaped core wrap 40b.

A liquid-permeable top sheet 50 is provided on the front surface side (skin contact surface side) of the absorber 40. In addition, a liquid-impermeable back sheet 60a is provided on the rear surface side (non-skin contact surface side) of the absorber 40. An exterior sheet 60 is provided on the rear side of the back sheet 60a. The front edge of the back sheet is positioned at a rear side of the front edge of the disposable diaper, and the rear edge of the back sheet is positioned at a front side of the rear edge of the disposable diaper. Only the exterior sheet is disposed on the front edge and the rear edge of the disposable diaper, and the back film is not disposed thereon. Therefore, air permeability of the front edge and the rear edge of the disposable diaper is improved and steam is reduced, so that the delicate skin of the infant who is the wearer can be protected. In addition, since the front edge and the rear edge of the disposable diaper which easily hits the wearer's skin are not provided with the back film and are constituted by only the exterior sheet, it is possible to suppress the stimulation to the skin by the front edge and the rear edge of the disposable diaper. Since the number of layers of the front edge and the rear edge of the disposable diaper is small and the rigidity of the front edge and the rear edge of the disposable diaper is low, mothers have an overall gentle impression of the disposable diapers on the skin and can reduce the stress to the skin stimulation.

Side flaps 70 are provided on the outer edge (outer end in the width direction) of the absorber 40, respectively. The side flaps 70 are disposed over the front waistline region 20, the crotch region 25, and the rear waistline region 30 and at the outer side of the absorber 40 in the width direction. The side flaps 70 are constituted by one or two or more nonwoven fabrics stacked.

The side flaps 70 are provided with a pair of leg stretchable portions 75 which are disposed at the inner side of the leg surrounding opening 131 in the width direction and are stretchable in the longitudinal direction L. The leg stretchable portions 75 are arranged at the inner side of the left and right leg surrounding openings in the width direction, respectively.

The pair of fastening tapes 90 extend in the width direction W in the rear waistline region 30 and are fastened to the non-skin contact surface of the front waistline region 20, whereby the disposable diaper 10 is held on the wearer's body. The fastening tape 90 is attached to the region of the side flap 70 corresponding to the rear waistline region 30. The outer shape of the fastening tape is curved and does not have a sharp pointed shape. Therefore, the mother is not concerned about being stimulated by the fastening tape, and the anxiety about the stimulation to the skin is reduced.

A target portion 95 is provided on the non-skin contact side of the exterior sheet 60 of the front waistline region 20. The target portion 95 is configured such that the engagement hook of the fastening tape 90 is caught, and functions as a hook and a loop of a loop locking system. As the target portion 95, for example, an air-through nonwoven fabric can be used. This makes it possible to finish the disposable diaper softer and eliminate the sense of uneasiness of the mother that the delicate infant's skin will be damaged.

The disposable diaper 10 has a waist surrounding stretchable portion capable of expanding and contracting in the width direction. The waist surrounding stretchable portion 85 is arranged in the rear waistline region. The waist surrounding stretchable portion 85 is arranged between the pair of fastening tapes 90 in the width direction, and contracts in the width direction between the fastening tapes 90. The front edge of the waist surrounding stretchable portion 85 has a curved shape in which the width direction center is recessed rearward. This makes it possible to fit the rear end portion of the disposable diaper, on which the waist surrounding stretchable portion 85 is disposed, along the roundness of the buttocks of the wearer. In addition, since the waist surrounding stretchable portion is arranged in the rear waistline region, the rear waistline region is contracted by the waist surrounding stretchable portion, and wrinkles extending in the longitudinal direction are formed. In the rear waistline region, undulations that float in the thickness direction due to wrinkles are formed. The undulation makes it difficult for the outer edge of the disposable diaper (the first cutout portion, the second cutout portion and the like which will be described later) to be conspicuous, and the disposable diaper exerts a visual effect that gives a gentle impression to the skin as a whole, and mothers feel less stressful to the stimulation to the skin.

(2) Outer Edge Shape of Disposable Diaper

Figure 2:
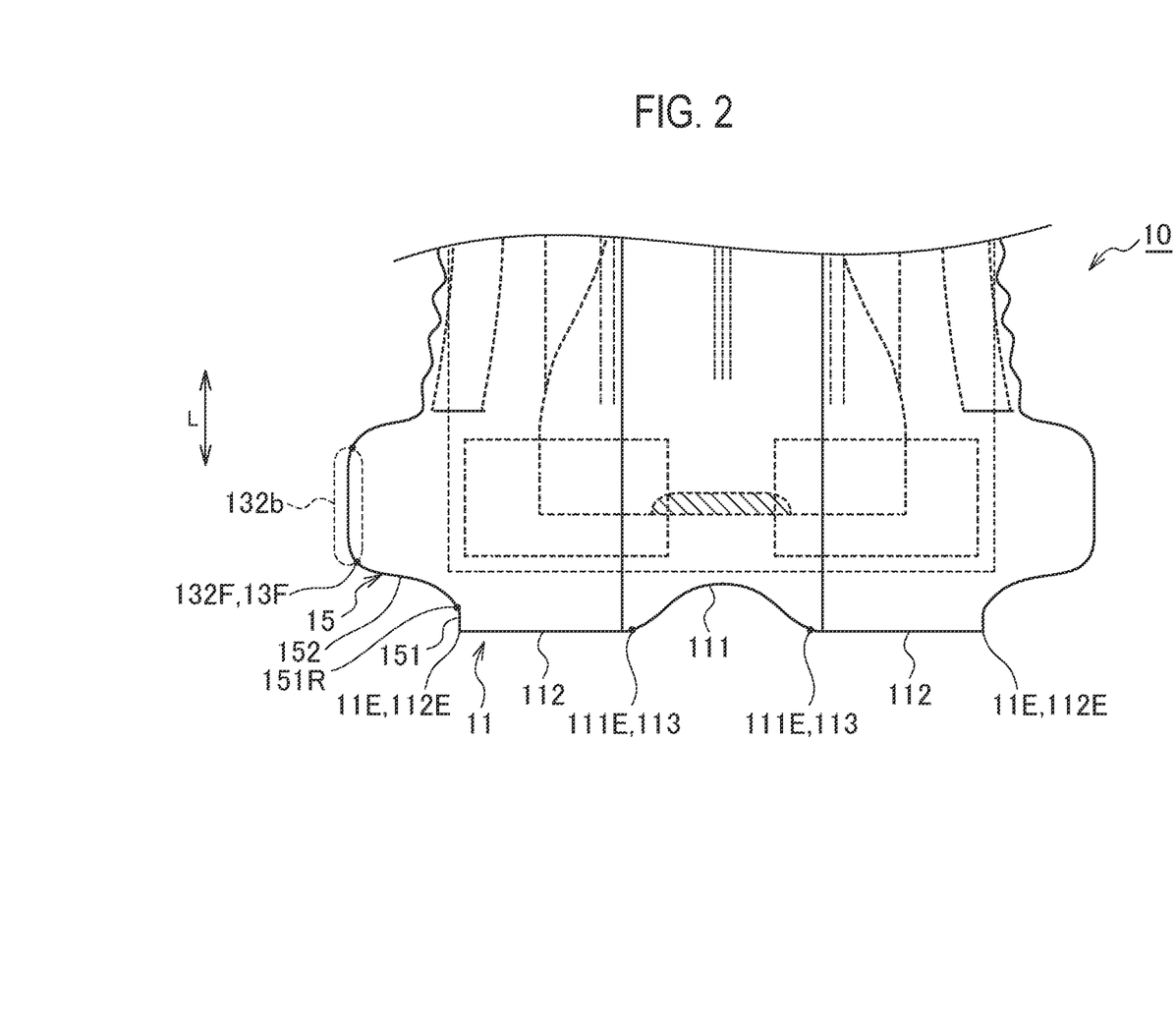
FIG. 2 is an enlarged plan view of a front edge of the disposable diaper illustrated in FIG. 1.
Figure 3:
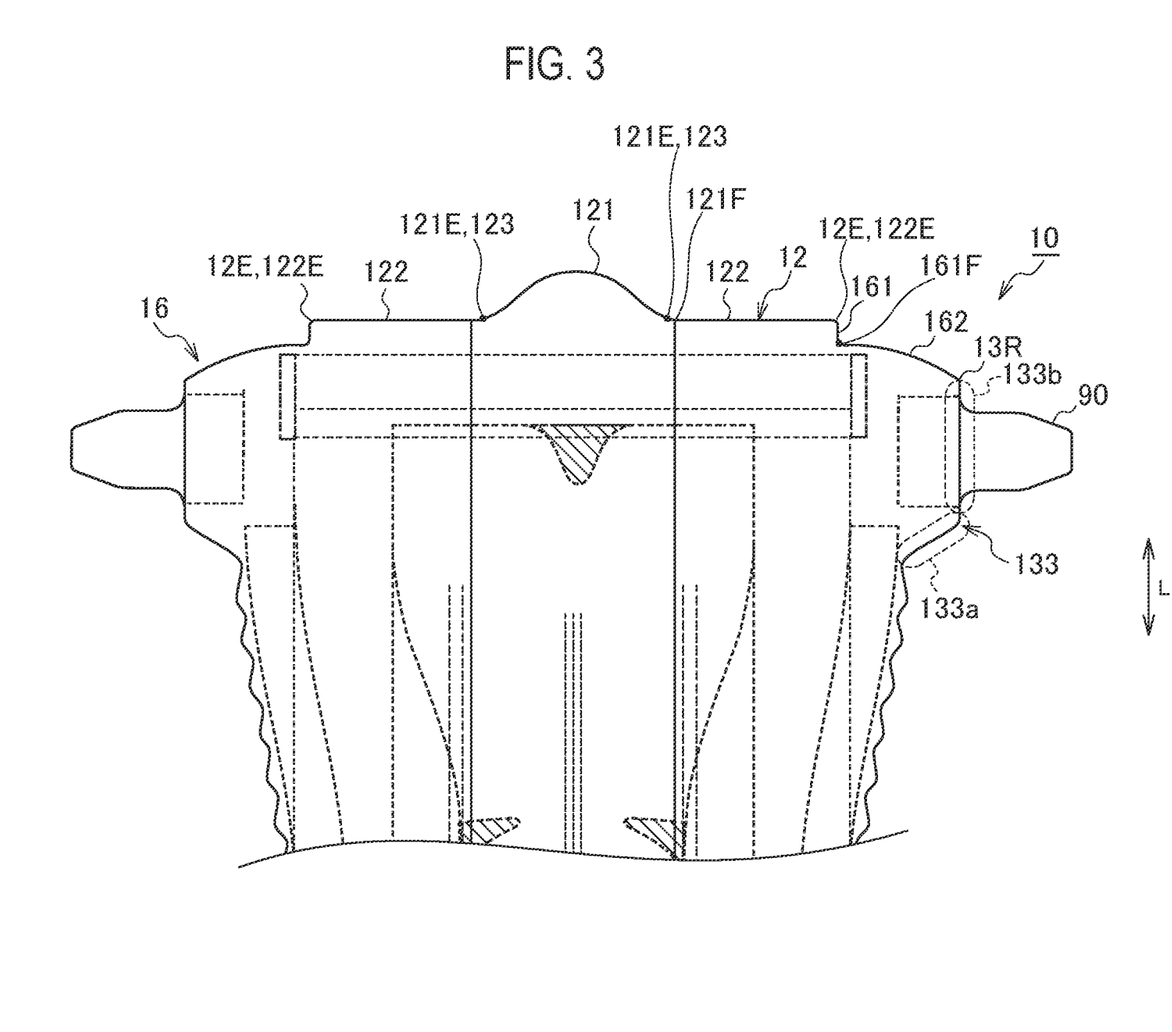
FIG. 3 is an enlarged plan view of a rear edge of the disposable diaper illustrated in FIG. 1.
Figure 4:
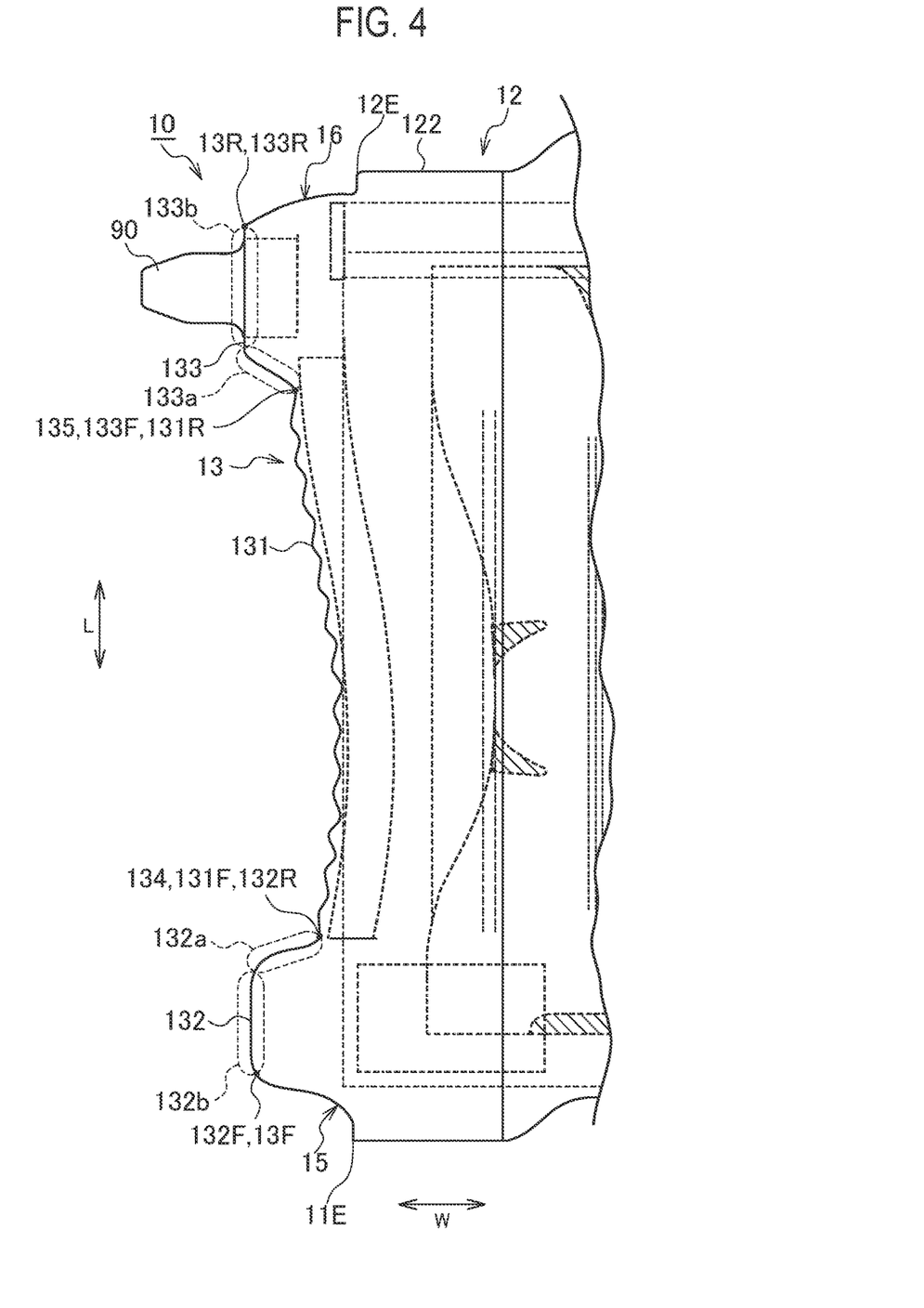
FIG. 4 is an enlarged plan view of an outer edge of the disposable diaper illustrated in FIG. 1.

Next, the shape of the outer edge of the disposable diaper will be described in detail. The outer edge shape in the following description is a shape in a stretched state (state illustrated in FIG. 1) of the disposable diaper. The outer edge of the disposable diaper is the contour of the disposable diaper in the planar state illustrated in FIG. 1. The outer edge of the disposable diaper is the outer edge of the sheet excluding the fastening tape, and includes a front edge 11, a rear edge 12, and a pair of outer edges 13. FIG. 2 is an enlarged plan view of the front edge 11 of the disposable diaper. FIG. 3 is an enlarged plan view of the rear edge 12 of the disposable diaper. FIG. 4 is an enlarged plan view of the outer edge 13 of the disposable diaper.

The front edge 11 of the disposable diaper extends in the width direction W and includes a recess 111 and front straight portions 112 arranged on both sides of the recess 111. The recess 111 and the front straight portion 112 are continuous. The recess 111 is provided in a region including the center in the width direction. The recess 111 has a shape that is recessed rearward and is formed in a curved shape. The width of the recess 111 narrows toward the rear. The front straight portion 112 extends parallel to the width direction from the outer edge 111E of the recess 111 toward the outer side in the width direction W. The inner edge of the front straight portion 112 is the outer edge 111E of the recess 111, and becomes the first intersection portion 113 where the recess 111 and the front straight portion 112 intersect. The outer edge 112E of the front straight portion 112 is the outer edge 11E at the front edge 11 of the disposable diaper. The curved recess makes it difficult for the ends of the disposable diaper in the longitudinal direction to hit the belly of the delicate infant, thus protecting the navel while suppressing the stimulation to the wearer's skin. The ventral side of the wearer is in an inflated shape as compared to the dorsal side, and the front edge of the disposable diaper is arranged thereon. The front edge of the disposable diaper is arranged with a cutout portion and a front straight portion extending parallel to the width direction and does not protrude outward in the longitudinal direction. Therefore, there is little stimulation when the front edge of the disposable diaper hits the inflated belly of the wearer, and it is possible to protect the delicate infant's skin. The mother has a gentle impression on the skin due to the curved recess, and can reduce the stress to the skin stimulation. In addition, the front edge of the disposable diaper extends parallel to the width direction from the recess and does not protrude outward in the longitudinal direction. Therefore, the stimulation to the skin by the front edge of the disposable diaper can be suppressed.

The rear edge 12 of the disposable diaper extends in the width direction W and includes a projection 121 and rear straight portions 122 arranged on both sides of the projection 121. The projection 121 and the rear straight portion 122 are continuous. The projection 121 is provided in a region including the center in the width direction. The projection 121 has a shape that protrudes rearward and is formed in a curved shape. The width of the projection 121 narrows toward the rear. The rear straight portion 122 extends parallel to the width direction from the outer 121E of the projection 121 toward the outer side in the width direction W. The inner edge of the rear straight portion 122 is the outer edge 121E of the projection 121, and becomes the second intersection portion 123 where the projection 121 and the rear straight portion 122 intersect. The outer edge 122E of the rear straight portion 122 is the outer edge 12E at the rear edge 12 of the disposable diaper. A spine is arranged in the center of the back of the wearer, and the center of the back of the wearer is recessed towards the ventral side from the left and right parts. The concave portion (rhombus of Michael) is a recess of a sacrum portion, and the projection is arranged therein. It is possible to cover the concave portion of the back and both sides thereof by the projection and the rear straight portion and prevent leakage on the dorsal side. The rear edge of the disposable diaper is arranged with a projection and a rear straight portion extending parallel to the width direction and does not protrude outward in the longitudinal direction. Therefore, there is little stimulation when the wearer is placed on the rear waistline region at the time of wearing and the rear edge of the disposable diaper hits the inflated back of the wearer, and it is possible to protect the delicate infant's skin. Since the relatively hard spine and the surrounding projection thereof have a shape that protrudes in a curved shape, mothers have a gentle impression on the skin and can reduce stress on the stimulation to the skin.

The outer edge 13 of the disposable diaper extends in the longitudinal direction, and includes a leg surrounding opening 131, a front flap portion 132 arranged in front of the leg surrounding opening, and a rear flap portion 133 arranged at a rear side of the leg surrounding opening 131. The front flap portion 132, the leg surrounding opening 131, and the rear flap portion 133 are continuous. The leg surrounding opening 131 is arranged at least in the crotch region 25. The leg surrounding opening 131 is arranged around the wearer's legs. The leg surrounding opening 131 has a shape that is recessed toward the inside in the width direction. Therefore, it is difficult to inhibit the movement of the legs of the wearer by the leg surrounding opening, and it is possible to reduce the stimulation to the skin by the leg surrounding opening.

The front flap portion 132 includes a first front flap portion 132a extending forward from the leg surrounding opening 131 and extending outward in the width direction, and a second front flap portion 132b extending forward from the outer edge (front edge) of the first front flap portion 132a. The front flap portion 132 extends forward from the front edge 131F of the leg surrounding opening 131 and extends outward in the width direction.

The position of the third intersection portion in the width direction and the position of the fourth intersection portion in the width direction may be shifted in the width direction. In the third intersection portion and the fourth intersection portion where the leg surrounding opening and the flap portion intersect, both the force related to the flap portion and the force related to the portion around the leg are applied, and thus the forces tend to concentrate. According to such a disposable diaper, the position of the third intersection portion in the width direction and the position of the fourth intersection portion in the width direction are not arranged on a straight line extending in parallel to the longitudinal direction, and the force applied to the third intersection portion and the force applied to the fourth intersection portion hardly concentrate, thereby suppressing the stimulation to the skin due to the concentration of the force. In addition, the front flap portion 132 extends outward in the width direction from the front edge of the leg surrounding opening 131. Therefore, when the wearer is placed on the rear waistline region at the time of wearing and attracts the front waistline region from the crotch of the wearer to the ventral side of the wearer, the wearer's legs can be hooked on the front flap portion 132, and the position of the front waistline region when worn is stable. Since the position of the front waistline region is stable when worn, there is no fear that the front waistline region moves unintentionally and stimulates the skin, and it is possible to eliminate mother's anxiety about skin stimulation.

The rear flap portion 133 extends rearward from the rear edge 131R of the leg surrounding opening 131 and extends outward in the width direction. In addition, the rear flap portion 133 extends outward in the width direction from the rear edge 131R of the leg surrounding opening 131. The rear flap portion 133 includes a first rear flap portion 133a extending rearward from the leg surrounding opening 131 and extending outward in the width direction, and a second rear flap portion 133b extending rearward from the outer edge (rear edge) of the first rear flap portion 133a. Therefore, when the wearer is placed on the rear waistline region during wearing, the rear flap portion is likely to be arranged at the outside of the wearer in the width direction. It is not necessary to draw the outer edge of the front waistline region from under the wearer's body after placing the wearer in the front waistline region, and it is possible to prevent the disposable diaper from rubbing against the wearer's skin.

The front edge 132F of the front flap portion 132 is the front edge 13F at the outer edge of the disposable diaper. The rear edge 132R of the front flap portion 132 is the front edge 131F of the leg surrounding opening 131, and is the third intersection portion 134 where the first front flap portion 132a and the leg surrounding opening 131 intersect. The rear edge 132R of the rear flap portion 133 is the rear edge 13R at the outer edge of the disposable diaper. The front edge 133F of the rear flap portion 133 is the rear edge 131R of the leg surrounding opening 131, and is the fourth intersection portion 135 where the first rear flap portion 133a and the leg surrounding opening 131 intersect. The rear edge 133R of the rear flap portion 133 is the rear edge 13R at the outer edge 13 of the disposable diaper.

The first intersection portion 113, the second intersection portion 123, the third intersection portion 134, and the fourth intersection portion 135 are curved in plan view. That is, the first intersection portion 113, the second intersection portion 123, the third intersection portion 134, and the fourth intersection portion 135 have a shape that does not have pointed corners and straight lines. Since the first intersection portion and the second intersection portion have a curved shape, it is possible to suppress the stimulation to the delicate navel or the hard portion of the spine. Since the third intersection portion and the fourth intersection portion have a curved shape, pointed corners are not formed at the front edge and the rear edge of the leg surrounding opening. Even when the wearer moves the legs and the leg surrounding opening strongly hits the wearer, it is possible to suppress the stimulation to the portion around the wearer's legs.

The disposable diaper includes: a pair of first cutout portions 15 recessed in a curved shape rearward from the outer edge 112E of the front straight portion 112 and recessed in a curved shape inward in the width direction from the front edge 13F of the outer edge 13 of the disposable diaper; and a pair of second cutout portions 16 recessed in a curved shape frontward from the outer edge 122E of the rear straight portion 122 and recessed in a curved shape inward in the width direction from the rear edge 13R of the outer edge 13 of the disposable diaper. As illustrated in FIG. 2, the first cutout portion 15 is provided between the outer edge 11E of the front edge 11 and the front edge 13F at the outer edge 13. The inner edge of the first cutout portion 15 coincides with the outer edge 11E of the front edge 11 of the disposable diaper. The first cutout portion 15 includes a first extension portion 151 extending rearward from the front straight portion 112, and a first width extension portion 152 extending rearward from the rear edge 151R of the first extension portion 151 and extending outward in the width direction. The first extension portion 151 extends parallel to the longitudinal direction L. The first extension portion 151 may extend rearward from the front straight portion 112 in parallel to the front-back direction, and may extend outward in the width direction as going rearward from the front straight portion 112. That is, the first extension portion 151 does not extend inward in the width direction from the front straight portion 112. The first width extension portion 152 is connected to the second front flap portion 132b. The first cutout portion does not have a pointed shape on the outer side in the longitudinal direction and can suppress the stimulation to the skin by the first cutout portion.

As illustrated in FIG. 3, the second cutout portion 16 is provided between the outer edge 12E of the rear edge 12 and the rear edge 13R at the outer edge 13. The inner edge of the second cutout portion 16 coincides with the outer edge 12E of the rear edge 12 of the disposable diaper. The second cutout portion 16 includes a second extension portion 161 extending frontward from the rear straight portion 122, and a second width extension portion 162 extending frontward from the front edge 161F of the second extension portion 161 and extending outward in the width direction. The second extension portion 161 extends parallel to the longitudinal direction. The second extension portion 161 may extend frontward from the rear straight portion 122 in parallel to the front-back direction, and may extend outward in the width direction as going frontward from the rear straight portion 122. That is, the second extension portion 161 does not extend inward in the width direction from the rear straight portion 122. The second width extension portion 162 is connected to the second rear flap portion 133b. Since the second cutout portion does not have a pointed shape on the outer side in the longitudinal direction, the stimulation to the skin by the second cutout portion can be suppressed. In addition, the four corners, the front edge, and the rear edge of the disposable diaper are not provided with a pointed shape on the outer side in the longitudinal direction, mothers have an overall gentle impression of the disposable diapers on the skin and can reduce the stress to the skin stimulation.

The first cutout portion 15 and the second cutout portion 16 constituting four corners of the disposable diaper are recessed inward in the longitudinal direction in a curved shape and are recessed inward in the width direction in a curved shape. Therefore, the first cutout portion and the second cutout portion do not have a pointed shape on the outer side in the longitudinal direction and can suppress the stimulation to the skin by the first cutout portion and the second cutout portion.

In addition, the front edge of the disposable diaper and the rear edge of the disposable diaper are arranged to overlap each other in a state in which the fastening tape is fastened. At this time, since the first cutout portion and the second cutout portion are recessed inward in the width direction, the outer edge of the rear edge of the disposable diaper does not overlap the outer edge of the front edge of the disposable diaper and is easily arranged spaced apart in the width direction. In addition, as illustrated in FIG. 4, the inner edge of the first cutout portion is positioned inside in the width direction than the imaginary line extending forward from the front edge 131F of the leg surrounding opening 131. That is, the first cutout portion 15 is recessed inward in the width direction from the front edge 131F of the leg surrounding opening 131. The inner edge of the second cutout portion 16 is positioned inside in the width direction than the imaginary line extending rearward from the rear edge 131R of the leg surrounding opening 131. That is, the second cutout portion 16 is recessed inward in the width direction from the rear edge 131R of the leg surrounding opening 131. Therefore, when the front edge and the rear edge of the leg surrounding opening overlap along the wearer's legs at the time of wearing, it is difficult for the outer edge of the rear edge of the disposable diaper to overlap the outer edge of the front edge of the disposable diaper, and it is easy to place them apart in the width direction. Therefore, air permeability is improved, steam is suppressed, and skin troubles such as eczema can be suppressed. In a case where the outer edge of the rear edge of the disposable diaper overlaps the outer edge of the front edge of the disposable diaper, since the first cutout portion is covered with the rear waistline region, it tends to directly touch the wearer's skin. Since the first cutout portion has a curved concave shape, the stimulation to the skin at the time of wearing can be suppressed.

When manufacturing such a disposable diaper, continuous sheets in which a front waistline region, a crotch region, and a rear waistline region in a plurality of disposable diapers are continued in a longitudinal direction are conveyed, and the continuous sheets are cut with a cutting line extending in the width direction, thereby manufacturing the plurality of disposable diapers. In a state of the continuous sheet in the manufacturing method, the first extension portion and the second extension portion are continuous, and the first extension portion of one disposable diaper and the second extension portion of the adjacent disposable diaper are formed by cutting at the cutting line. Since the first extension portion and the second extension portion extend parallel to the longitudinal direction, even when the cutting position deviates in the longitudinal direction during the manufacture, it is possible to prevent an unintentional formation of an acute angle in the first cutout portion and the second cutout portion, without a change in the angle of the first cutout portion and the second cutout portion.

(3) Modification

Figure 5:
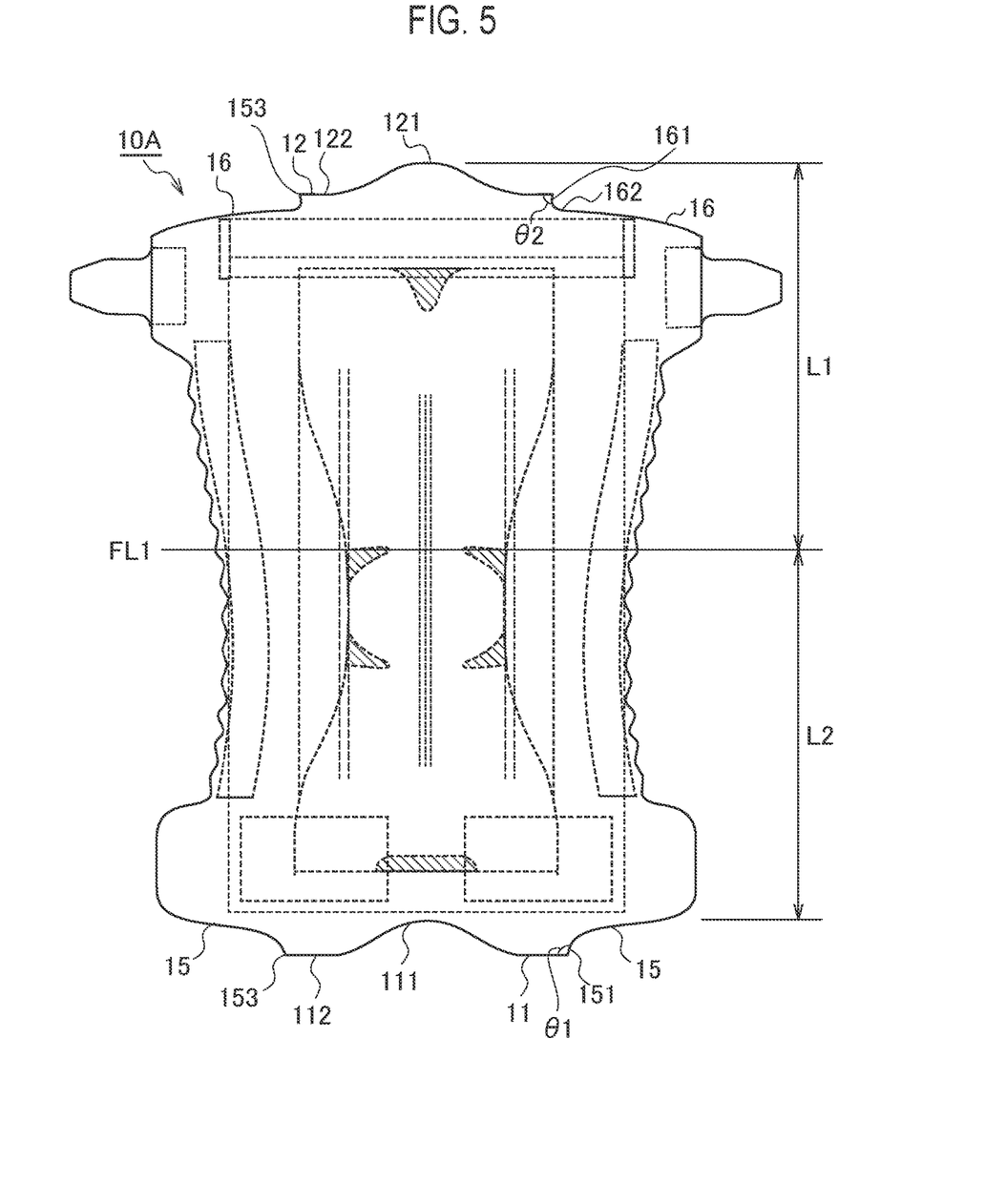
FIG. 5 is a developed plan view of a disposable diaper according to a modification.

Next, a disposable diaper according to a modification will be described with reference to FIG. 5. In the description of the modification, the same reference symbols are used for the same configurations as in the above-described embodiment, and a description thereof is omitted. An angle θ1 formed between the front straight portion 112 and the first extension portion 151 at the front edge 11 of the disposable diaper according to the modification is an obtuse angle. The first extension portion 151 extends outward in the width direction as going rearward from the front straight portion 112. In addition, an angle θ2 formed between the rear straight portion 122 and the second extension portion 161 at the rear edge 12 of the disposable diaper is an acute angle. The second extension portion 161 extends outward in the width direction as going frontward from the rear straight portion 122. The fifth intersection portion 153 where the rear straight portion 122 and the second extension portion 161 intersect may have a pointed shape toward the outside in the width direction. The fifth intersection portion 153 is not pointed toward the outside in the longitudinal direction. In addition, since the first cutout portion has an obtuse angle, the stimulation to the skin can be suppressed. In addition, it gives an impression that it is gentle to the wearer's belly, and stress of the mother on the stimulation to the skin can be reduced. In addition, the second cutout portion is arranged to overlap the front waistline region when the fastening tape is fastened, and does not directly touch the wearer's skin. Therefore, the stimulation to the wearer's skin can be prevented even if the fifth intersection portion where the rear edge of the disposable diaper and the second cutout portion intersect is an acute angle.

In addition, the disposable diaper according to the modification has the folding line FL1 extending in the width direction. The folding line FL1 is arranged in the crotch region 25 and extends parallel to the width direction W. The disposable diaper is accommodated in a package in a state being two-folded at least by a folding line. A distance L1 in the longitudinal direction between the folding line FL1 and the width direction center of the projection 121 is longer than a distance L2 in the longitudinal direction between the folding line FL1 and the width direction center of the recess 111. Therefore, the projection extends outward in the longitudinal direction than the recess in a state of being folded with the folding line as a base point. In a state in which a plurality of disposable diapers are stacked, a wearing assistant such as a mother can easily take out the disposable diaper by gripping the projection.

While the contents of the present invention have been described through the embodiments described above, it should not be understood that the description and drawings constituting a part of this disclosure limit the present application. From this disclosure, various alternative embodiments, examples, and operational technologies will become apparent to those skilled in the art. Therefore, the technical scope of the present invention is determined only by the invention specifying matters pertaining to the claims proper from the above description.

The entire contents of Japanese Patent Application No. 2016-17174, filed on Feb. 1, 2016, are incorporated hereby by reference.

INDUSTRIAL APPLICABILITY

It is possible to provide a disposable diaper which can protect the navel while suppressing the stimulation to the wearer's skin and can reduce stress of mothers on the stimulation to the skin.

REFERENCE SIGNS LIST

| 10, 10A | disposable diaper | | |
|---|---|---|---|
| 20 | front waistline region | | |
| 25 | crotch region | | |
| 30 | rear waistline region | | |
| 40 | absorber | | |
| 11 | front edge, | 11E | outer edge |
| 111 | recess, | 111E | outer edge |
| 112 | front straight portion, | 112E | outer edge |
| 12 | rear edge, | 12E | outer edge |
| 121 | projection, | 121E | outer edge |
| 122 | rear straight portion, | 122E | outer edge |
| 13 | outer edge | | |
| 131 | leg surrounding opening | | |
| 132 | front flap portion, | 132a | first front flap portion, |
| 132b | second front flap portion | | |
| 133 | rear flap portion, | 133a | first rear flap portion, |
| 133b | second rear flap portion | | |
| 15 | first cutout portion | | |
| 151 | first extension portion | | |
| 152 | first width extension portion | | |
| 16 | second cutout portion | | |
| 161 | second extension portion | | |
| 162 | second width extension portion | | |
| 113 | first intersection portion | | |
| 123 | second intersection portion | | |
| 134 | third intersection portion | | |
| 135 | fourth intersection portion | | |
| L | longitudinal direction | | |
| W | width direction | | |

The invention claimed is:

1. A disposable diaper comprising:
a front waistline region, a rear waistline region, and a crotch region positioned between the front waistline region and the rear waistline region;
a longitudinal direction extending from the front waistline region to the rear waistline region and a width direction perpendicular to the longitudinal direction; and
a pair of fastening tapes extending in the width direction in the rear waistline region and fastened to the front waistline region,
wherein the front edge of the disposable diaper includes a curved recess recessed rearward in a region including the center of the disposable diaper in the width direction, and a front straight portion extending parallel to the width direction from the outer edge of the recess, and
the rear edge of the disposable diaper includes a curved projection protruding rearward in the region including the center of the disposable diaper in the width direction, and a rear straight portion extending parallel to the width direction from the outer edge of the projection,
the disposable diaper comprising:
a pair of first cutout portions recessed rearward in a curved shape from the outer edge of the front straight portion and recessed inward in the width direction in a curved shape from the front edge of the outer edge of the disposable diaper; and
a pair of second cutout portions recessed frontward in a curved shape from the outer edge of the rear straight portion and recessed inward in the width direction in a curved shape from the rear edge of the outer edge of the disposable diaper.

2. The disposable diaper according to claim 1, wherein the disposable diaper comprises a first intersection portion where the recess and the front straight portion intersect with each other and a second intersection portion where the projection and the rear straight portion intersect with each other, and the first intersection portion and the second intersection portion have a curved shape.

3. The disposable diaper according to claim 1, wherein the outer edge of the disposable diaper comprises a leg surrounding opening arranged around the wearer's leg, a front flap portion arranged in front of the leg surrounding opening, and a rear flap portion arranged at a rear side of the leg surrounding opening, and a third intersection portion where the leg surrounding opening and the front flap portion intersect and a fourth intersection portion where the leg surrounding opening and the rear flap portion intersect have a curved shape.

4. The disposable diaper according to claim 3, wherein the fourth intersection portion is positioned outside the third intersection portion in the width direction.

5. The disposable diaper according to claim 1, wherein the first cutout portion comprises a first extension portion extending rearward from the front straight portion, the second cutout portion comprises a second extension portion extending frontward from the rear straight portion, an angle formed by the front straight portion and the first extension portion is an obtuse angle, an angle formed by the rear straight portion and the second extension portion is an acute angle, and a fifth intersection portion where the rear straight portion and the second extension portion intersect has a pointed shape toward the outside in the width direction.

6. The disposable diaper according to claim 1, wherein the first cutout portion comprises a first extension portion extending rearward from the front straight portion, the second cutout portion comprises a second extension portion extending frontward from the rear straight portion, and the first extension portion and the second extension portion extend parallel to the longitudinal direction.

7. The disposable diaper according to claim 1, wherein the disposable diaper comprises a waist stretchable portion which is arranged in the rear waistline region of the disposable diaper and expands and contracts in the width direction.

8. The disposable diaper according to claim 1, wherein a folding line extending in the width direction is provided in the crotch region, and a distance in the longitudinal direction between the folding line and the width direction center of the projection is longer than a distance in the longitudinal direction between the folding line and the width direction center of the recess.

9. The disposable diaper according to claim 1, wherein the disposable diaper comprises:

a back film arranged on a non-skin surface side of the absorber; and an exterior sheet made of a nonwoven fabric and positioned on the non-skin surface side of the back film, wherein a front edge of the back film is positioned at a rear side of the front edge of the disposable diaper, and a rear edge of the back film is positioned at a front side of the rear edge of the disposable diaper.

* * * * *